(12) United States Patent
Goto et al.

(10) Patent No.: US 8,568,745 B2
(45) Date of Patent: Oct. 29, 2013

(54) WATER-SOLUBLE DRUG CARRIER AND PROCESS FOR PRODUCING THE SAME

(75) Inventors: Masahiro Goto, Fukuoka (JP); Noriho Kamiya, Fukuoka (JP); Yoshiro Tahara, Fukuoka (JP)

(73) Assignee: Kyushu University, National University Corporation, Fukuoka-shi (JP)

( * ) Notice: Subject to any disclaimer, the term of this patent is extended or adjusted under 35 U.S.C. 154(b) by 0 days.

(21) Appl. No.: 13/382,705

(22) PCT Filed: Jun. 16, 2010

(86) PCT No.: PCT/JP2010/004021
§ 371 (c)(1),
(2), (4) Date: Apr. 26, 2012

(87) PCT Pub. No.: WO2011/004552
PCT Pub. Date: Jan. 13, 2011

(65) Prior Publication Data
US 2012/0207794 A1    Aug. 16, 2012

Related U.S. Application Data

(60) Provisional application No. 61/224,171, filed on Jul. 9, 2009.

(51) Int. Cl.
*A61K 9/00* (2006.01)
*A61K 38/18* (2006.01)
*A61K 31/711* (2006.01)

(52) U.S. Cl.
USPC .......................................... 424/400; 514/9.6

(58) Field of Classification Search
None
See application file for complete search history.

(56) References Cited

U.S. PATENT DOCUMENTS

2010/0297222 A1* 11/2010 Kanaya et al. ............. 424/455
2010/0298447 A1* 11/2010 Fujii et al. .................. 514/783

FOREIGN PATENT DOCUMENTS

| JP | 07-255478 A | 10/1995 |
| JP | 2004-008837 A | 1/2004 |
| JP | 2004-043355 A | 2/2004 |
| JP | 2006-504636 A | 2/2006 |
| JP | 2007-119436 A | 5/2007 |
| JP | 2008-508302 A | 3/2008 |
| WO | WO-03/101600 A2 | 12/2003 |
| WO | WO-03/101600 A3 | 12/2003 |
| WO | WO-2006/015120 A2 | 2/2006 |
| WO | WO-2009/057808 A1 | 5/2009 |
| WO | WO-2009/060609 A1 | 5/2009 |

OTHER PUBLICATIONS

IA Khalil et al., "Octaarginine-modified multifunctional envelope-type nanoparticles for gene delivery," Gene Therapy, 2007, vol. 14, pp. 682-689.
International Search Report dated Sep. 7, 2010, issued for PCT/JP2010/004021.

* cited by examiner

*Primary Examiner* — Robert A Wax
*Assistant Examiner* — Danah Al-Awadi
(74) *Attorney, Agent, or Firm* — Edwards Wildman Palmer LLP

(57) ABSTRACT

An object of the present invention is to provide a drug delivery carrier that is free from the drug leakage problem and has an easily controllable particle size, and that can be used to deliver water-soluble drugs such as genes and proteins in a wide range of applications, including delivery of water-soluble drugs that do not have high anionic properties, and also can be used as a non-viral gene vector. The invention also provides a process for production of such drug delivery carriers. The drug delivery carrier of the present invention includes a water-soluble drug double-coated with two types of inner and outer surfactants 1 and 2.

5 Claims, 8 Drawing Sheets

EFFECTS OF SURFACTANT WEIGHT RATIO

EFFECTS OF ADDING DOPE

S/O PARTICLE SIZE (A)

(B)

S/W PARTICLE SIZE (C)

(D)

PARTICLE SIZE OF pDNA-ENCAPSULATED S/O AND S/W
(A, C: DLS MEASUREMENTS; B, D: TEM OBSERVATION)

ns, are typical known examples of water-soluble drug
WATER-SOLUBLE DRUG CARRIER AND PROCESS FOR PRODUCING THE SAME

TECHNICAL FIELD

The present invention relates to drug delivery carriers capable of delivering water-soluble drugs such as genes and proteins, and to a novel drug delivery carrier produced by double-coating a solid dispersion of a water-soluble drug with different amphiphatic molecules (two types of surfactants), and to a process for production of such drug delivery carriers.

BACKGROUND ART

This application claims the priority of U.S. Provisional Application No. 61/224,171 filed Jul. 9, 2009, the contents of which are hereby incorporated by reference.

Liposomes and Water-in-Oil-in-Water (W/O/W) emulsions are typical known examples of water-soluble drug delivering carriers. However, these carriers are problematic because they involve drug leakage and difficulties in controlling the particle size.

Meanwhile, along with the developments in biotechnology, there have been active attempts to deliver various substances into a target cell, including peptides involved in the cellular signal transduction system, proteins having physiologically important roles in the cell, and expression genes for these products. It is often the case that the expression genes are more suited for delivery into the cell than the product proteins. The reasons for this include the simpler structure (genes do not have as large differences as proteins in overall structures and properties even when the proteins they express are different), good expectancy for lasting efficacy after the introduction into the cell, and no risk posed by the expression genes themselves, even though the expressed proteins may involve a risk or a pathogenic factor. The genes used for this purpose may be genes administered to cause expression of proteins lacking in a diseased cell, or genes that can induce cell death, such as caspase and thymidine kinase expression genes. There have been attempts to use genes themselves as drugs. It is therefore believed that the development of gene vectors having high expression efficiency (gene carriers with high gene introducibility into a cell and high expressibility) or control systems for such gene vectors have important roles in future medical developments (Non-Patent Document 1).

Administration of a gene alone into a cell produces only marginal expression efficiency. This is known to be primarily due to the high anionic properties of the cell membrane structure that includes sugar chains such as proteoglycan. The DNA molecule, as the building block of genes, is a polymer that also has anionic properties. At present, virus vectors produced by inserting or replacing a therapeutic gene into the gene sequence of viruses such as adenovirus and retrovirus represent the most efficient gene vectors. The virus vector takes advantage of the inherent characteristics of the viruses carrying their own genes into a cell, and can achieve high-efficient gene expression; however, its development is limited by safety and productivity (Non-Patent Document 2). As a countermeasure, there have been active studies to create non-viral gene vectors, as represented by, for example, cationic liposome. The commercially available Lipofectamine and Lipofectin, in particular, have become the most mainstream non-viral gene vectors, because these gene vectors have high gene introduction efficiency, and are highly useful and reproducible for many types of cells (Non-Patent Document 3). Aside from these examples, it is known that cationic polymers such as polyethyleneimine (Non-Patent Document 4) and chitosan (Non-Patent Document 5), and amino acid dendrimers (Non-Patent Document 6) also can be used for gene expression. All of these examples are based on the concept that the genes having anionic properties form a complex with the cationic molecules and break through the negatively charged cell membrane. However, these techniques, by themselves, lack serum resistance and blood stability, pose difficulties for use in vivo, and are often limited for further functionalization. There have been attempts to construct a DNA-encapsulated capsule carrier for further functionalization, as described in Non-Patent Document 7 (Multifunctional Envelope-type Nano Device; MEND), and Non-Patent Documents 8 and 9 (polymer micelle). However, these techniques all use cationic molecules for gene encapsulation, and have drawbacks that controlling the expression of the introduced gene in a cell is difficult, and that the techniques are only applicable to the encapsulation of substances having high anionic properties.

CITATION LIST

Non-Patent Documents

Non-Patent Document 1: I. J. van Dillen, N. H. Mulder, W. Vaalburg, E. F. de Vries, G. A. Hospers, Curr. Opin. Mol. Ther. 2, 307-322 (2002).
Non-Patent Document 2: H. Akita, R. Ito, I. A. Khalil, S. Futaki, H Harashima, Mol Ther. 9, 443-451 (2004).
Non-Patent Document 3: K. Kostarelos, A. D. Miller, Chem. Soc. Rev. 34, 970-994 (2005).
Non-Patent Document 4: J. A. Hubbell, Gene Ther. 13, 1371-1372 (2006).
Non-Patent Document 5: D. C. Liang, W. G. Liu, A. J. Zuo, S. J. Sun, N. Cheng, G. Guo, J. Y. Zhang, K. D. Yao, Int. J. Pharm. 314, 63-71 (2006).
Non-Patent Document 6: M. Yamagata, T. Kawano, K. Shiba, T. Mori, Y. Katayama, T. Niidome, Bioorg. Med. Chem. 15, 526-532 (2007).
Non-Patent Document 7: I. A. Khalil, K. Kogure, S. Futaki, S. Hama, H. Akita, M. Ueno, H. Kishida, M. Kudoh, Y. Mishina, K. Kataoka, M. Yamada, H. Harashima, Gene Ther. 14, 682-689 (2007).
Non-Patent Document 8: S. Takae, K. Miyata, M. Oba, T. Ishii, N. Nishiyama, K. Itaka, Y. Yamasaki, H. Koyama, K. Kataoka, J. Am. Chem. Soc. 130, 6001-6009 (2008).
Non-Patent Document 9: M. Oba, K. Aoyagi, K. Miyata, Y. Matsumoto, K. Itaka, N. Nishiyama, Y. Yamasaki, H. Koyama, K. Kataoka, Mol. Pharm. 5 1080-1092 (2008).
Non-Patent Document 10: Y. Tahara, S. Honda, N. Kamiya, H. Piao, A. Hirata, E. Hayakawa, T. Fujii, M. Goto, J. Control. Release 131, 14-18 (2008).
Non-Patent Document 11: N. Kanayama, S. Fukushima, N. Nishiyama, K. Itaka, W. D. Jang, K. Miyata, Y. Yamasaki, U. I. Chung, K. Kataoka, ChemMedChem 1, 439-444 (2006).

SUMMARY OF THE INVENTION

Problems that the Invention is to Solve

Accordingly, it is an object of the present invention to provide a drug delivery carrier that is free from the drug leakage problem and has an easily controllable particle size, and that can be used to deliver water-soluble drugs such as genes and proteins in a wide range of applications, including delivery of water-soluble drugs that do not have high anionic properties, and to provide a process for production of such drug delivery carriers.

Another object is to provide a drug delivery carrier that can be used as a non-viral gene vector, and a process for production thereof.

Means for Solving the Problems

In order to solve the foregoing problems, the present inventors conducted intensive studies, and found that a drug delivery carrier capable of delivering water-soluble drugs such as genes and proteins can be obtained by double-coating a solid dispersion of a water-soluble drug with different amphiphatic molecules, while providing an easily controllable particle size and without causing the drug leakage problem, regardless of whether the water-soluble drugs have high anionic properties.

The present invention has been completed based on this finding, and provides a drug delivery carrier that includes a water-soluble drug double-coated with two types of inner and outer surfactants 1 and 2.

Further, in the drug delivery carrier, the water-soluble drug is any one of protein, gene, oligonucleic acid, polysaccharide, synthetic polymer, peptide, small molecule, and nanoparticle (ultrastructure).

Further, in the drug delivery carrier, the gene is a plasmid DNA (hereinafter, "pDNA"), and the protein is an EGFP.

Further, in the drug delivery carrier, the inner surfactant 1 is any one of sucrose fatty acid ester, cholesterol, and glycerin fatty acid ester.

Further, in the drug delivery carrier, the outer surfactant 2 is at least one of PC, L-1695, PEG(2K)-MS, PEG(2K)-DSPE, PEG(5K)-DSPE, PEG(comb)-DSPE, Tween 80, sodium dodecyl sulfate, and glycerin fatty acid ester.

Further, in the drug delivery carrier, the drug delivery carrier includes at least one of hydrophobic molecules such as DOPE and dinitrochlorobenzene, and cationic polymers such as PEI and poly-L-lysine.

Further, in the drug delivery carrier, the drug delivery carrier is modified on the outside by a cell membrane protein binding domain, including alkylated transmembrane peptides (for example, such as stearyl octaarginine R8-str, and stearyl tetraarginine R4-str), N-hydroxysuccinimide-PEG (2K)-DSPE, N-maleimide-PEG(2K)-DSPE, N-hydroxysuccinimide-PEG(2K)-DSPE, and antibodies, saquinavir, and hyaluronic acid modified by these.

Further, the drug delivery carrier producing process of the present invention is a process for producing a drug delivery carrier that includes a water-soluble drug double-coated with two types of inner and outer surfactants 1 and 2, and includes the steps of:

1) mixing and agitating a water-soluble drug-containing aqueous phase with an oily phase containing the surfactant 1 to form a W/O emulsion in which the water-soluble drug-containing aqueous phase is dispersed in the oily phase;

2) removing the inner aqueous phase from the W/O emulsion to form a S/O in which the water-soluble drug-surfactant 1 complex is dispersed in the oily phase;

3) mixing and agitating the S/O with an aqueous phase containing the surfactant 2 to form a S/O/W emulsion in which the S/O is dispersed in the aqueous phase; and 4) removing the inner oily phase from the S/O/W emulsion to form a S/W in which the water-soluble drug-surfactant 1-surfactant 2 complex is dispersed in the aqueous phase.

Further, in the drug delivery carrier producing process, the inner aqueous phase and the inner oily phase are removed by freeze drying.

Further, in the drug delivery carrier producing process, the S/O/W emulsion is formed with addition or without addition of any one of glycerine, sorbitol, and trehalose.

Further, in the drug delivery carrier producing process, the S/O is formed in such a manner that at least one of hydrophobic molecules such as DOPE and dinitrochlorobenzene, and cationic polymers such as PEI and poly-L-lysine is contained in the S/W emulsion.

Further, in the drug delivery carrier producing process, the S/W is formed in such a manner that a cell membrane protein binding domain, including alkylated transmembrane peptides (for example, such as stearyl octaarginine R8-str, and stearyl tetraarginine R4-str), N-hydroxysuccinimide-PEG (2K)-DSPE, N-maleimide-PEG(2K)-DSPE, N-hydroxysuccinimide-PEG(2K)-DSPE, and antibodies, saquinavir, and hyaluronic acid modified by these is contained in the S/O/W emulsion.

The Solid-in-Oil (S/O) technique that produces a perfect solid dispersion of the encapsulated drug in a carrier by removing the inner aqueous phase from the W/O emulsion is the technique that enables the water-soluble drug to be stably dispersed in the oily base by coating the solid drug surface with a surfactant. By taking advantage of the S/O technique, the present invention uses the Solid-in-Water (S/W) technique that disperses a water-soluble drug in water using two types of surfactants by removing the inner oily phase from the Solid-in-Oil-in-Water (S/O/W) emulsion obtained by dispersing S/O preparation-dissolved oil droplets in water using another surfactant. The S/O is the state after removing the inner aqueous phase from the water-in-oil (W/O) emulsion in which water is dispersed in oil using a surfactant. In the S/O state, the drug is dispersed in the oil as a surfactant-drug complex (solid) with a surfactant coating. The solid-in-oil-in-water (S/O/W) emulsion results after dispersing the S/O in water using a new, different surfactant, and S/W is the state after removing the inner oily phase from the S/O/W emulsion. It is believed that the drug at the center is dispersed in water as a complex (solid) coated with the two kinds of surfactants. The S/W so prepared is believed to be an aggregate, best described as a liposome without an inner aqueous phase, and can be used as a carrier for delivering a water-soluble drug, and also as a non-viral gene vector after encapsulation of an appropriate functional molecule, or modification with an appropriate functional molecule.

The drug delivery carrier of the present invention is a carrier that includes a water-soluble drug double-coated with two types of surfactants 1 and 2.

The water-soluble drug is not limited to drugs with pharmacological activity in the narrow sense, but encompasses various labeling reagents such as fluorescence proteins. Specific examples include fluorescence proteins such as EGFP; proteins with pharmacological activity such as cytokines, antibodies, and gene transcription factors; genes such as pDNA; oligonucleic acids such as siRNA; polysaccharides such as dextran and hyaluronic acid; synthetic polymers; peptides such as octaarginine; small molecules such as diclofenac; and nanoparticles (or ultrastructures) such as a gold nanorod.

Examples of the inner surfactant 1 include sucrose fatty acid ester, cholesterol, and glycerin fatty acid ester.

Examples of the outer surfactant 2 include PC, L-1695, PEG(2K)-MS, PEG(2K)-DSPE, PEG(5K)-DSPE, PEG(comb)-DSPE, Tween 80, sodium dodecyl sulfate, and glycerin fatty acid ester.

The drug delivery carrier may contain hydrophobic molecules such as DOPE and dinitrochlorobenzene, or cationic polymers such as PEI and poly-L-lysine.

Further, the drug delivery carrier may be modified on the outside with a cell membrane protein binding domain, including alkylated transmembrane peptides (for example, such as stearyl octaarginine R8-str, and stearyl tetraarginine R4-str), N-hydroxysuccinimide-PEG(2K)-DSPE, N-maleimide-PEG(2K)-DSPE, N-hydroxysuccinimide-PEG(2K)-DSPE, and antibodies, saquinavir, and hyaluronic acid modified with these.

In the drug delivery carrier producing process of the present invention, it is preferable that the inner aqueous phase and the inner oily phase be removed by freeze drying.

Further, it is preferable that the S/O/W emulsion be formed with addition of glycerine or sorbitoltrehalose.

A drug delivery carrier containing, for example, DOPE or PEI can be easily obtained when the S/O is formed so as to contain at least one of hydrophobic molecules such as DOPE and dinitrochlorobenzene, and cationic polymers such as PEI and poly-L-lysine in the S/W emulsion.

Further, a drug delivery carrier modified with, for example, R8-str or R4-str on the outside can easily be obtained when the S/O/W emulsion in the step of forming the S/W contains a cell membrane protein binding domain, including alkylated transmembrane peptides (for example, such as stearyl octaarginine R8-str, and stearyl tetraarginine R4-str), N-hydroxysuccinimide-PEG(2K)-DSPE, N-maleimide-PEG(2K)-DSPE, N-hydroxysuccinimide-PEG(2K)-DSPE, and antibodies, saquinavir, and hyaluronic acid modified by these.

Advantage Of The Invention

The S/W drug delivery carrier of the present invention is advantageous over other drug carriers because (a) the carrier represents a whole collection system that does not require filtration, and thus the drug collectability is very high, (b) the carrier is obtained as a solid, and thus enables adjustments of final drug concentration, (c) the carrier can encapsulate drugs as long as the drugs can withstand the contact and agitation with an organic solvent, and the freeze drying during the emulsion preparation, and above all (d) the carrier enables the spatial relationship of the constituent components to be forcibly controlled using the W/O emulsion and the O/W emulsion, and thus ensures that the drug is always at the core (center) of the carrier, as compared to other carriers that encapsulate the drug only by the self-assembly of the constituent molecules.

EXAMPLES

The following describes the Examples of the present invention in detail. The scope of the present invention, however, is not limited to the Examples below.

Experiment Example 1

Surfactant Cytotoxicity

A cytotoxicity test was performed for phosphatidylcholine (PC; NOF Corporation), a constituent component of the cell membrane and usable as the water dispersible surfactant 2, and for sucrose laurate ester (L-1695), a hydrophilic surfactant. For the cytotoxicity test, a Cell Counting Kit-8 (Dojindo Molecular Technologies, Inc.), and a Luciferase Assay System (Promega) were used.

(1) B16 melanoma cells cultured in a D-MEM medium (Wako Pure Chemical Industries, Ltd.) were counted, and cultured overnight after being inoculated in a 96-well plate ($5 \times 10^3$ cells/well).

(2) The medium was removed, and the cells were cultured for 6 hours after each medium dissolving PC and L-1695 (0.10, 0.50, 1.0, 3.0 mg/mL) was added (100 μL/well). Here, wells containing only the medium (controls and blanks) were also prepared.

(3) The medium was removed after 6 hours from (2), and a WST-8 solution (containing 1-methoxy-PMS) was added to perform a color reaction for 2 hours. Absorbance at 450 nm was measured, and cell viability was determined relative to the control using the following formula 1.

Cell viability [%]=(Abs(450 nm)sample−Abs(450 nm) blank)/(Abs(450 nm)control−Abs(450 nm)blank)×100     (Formula 1).

Figure 1:
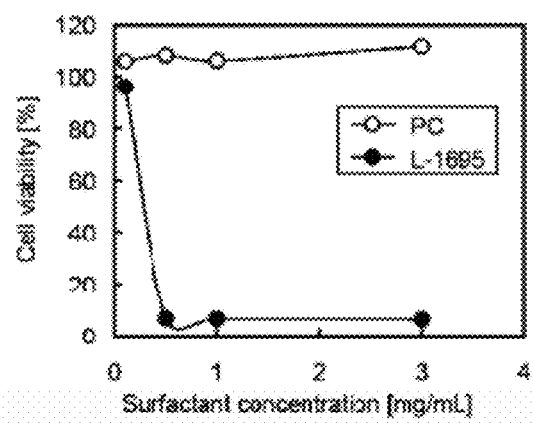
FIG. 1 is a graph representing surfactant cytotoxicity.

As can be seen from the result shown in FIG. 1, PC had no cytotoxicity, confirming that PC could be used to prepare a S/W preparation of low cytotoxicity. The result also confirmed that L-1695, at low concentrations, also could be used to prepare a S/W preparation of low cytotoxicity.

Experiment Example 2

Effects of Surfactant Weight Ratio

Surfactants that can produce S/O are generally hydrophobic, and accordingly the surfactant-drug complex in the S/O is also highly hydrophobic. Because it is this highly hydrophobic complex that is dispersed in water, the dispersibility of ER-290 in water with PC was confirmed by using a S/W prepared from an O/W emulsion containing cyclohexane (containing the hydrophobic surfactant ER-290 (sucrose erucate ester; Mitsubishi-Kagaku Foods Corporation)) and PC in water in varying ER-290:PC weight ratios (1:0, 1:1, 1:2, 1:3, 1:4, 1:5; the ER-290 weight was held constant).

(1) A PC-ER-290 complex solid was obtained by freeze drying the O/W emulsion prepared from 0.50 mL of a 10 mg/mL ER-290 cyclohexane solution, and 5.0 mL of a PC aqueous solution (0, 1.0, 2.0, 3.0, 4.0, 5.0 mg/mL).

(2) 2.0 mL of water was added to the solid (1), and the dispersibility was observed in each sample.

Figure 2:
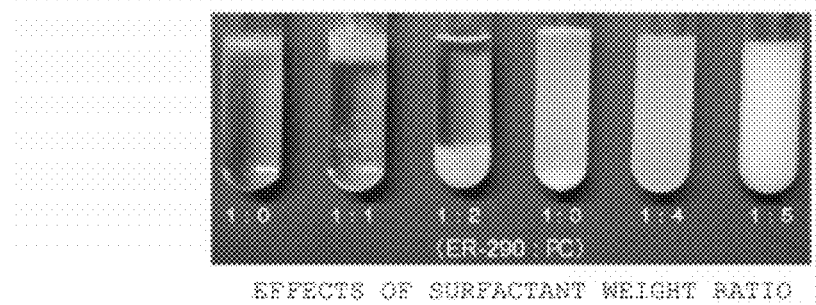
FIG. 2 is a photographic representation of the effects of surfactant weight ratio.

FIG. 2 shows the appearance of the resulting S/W. The white solid suspending in the upper part of the samples with the ER-290:PC weight ratios of 1:0 and 1:1 is the ER-290. It was found that such phase separation became smaller with increase in PC, and that the dispersion became uniform at ER-290:PC weight ratios above 1:4. These results thus confirmed that ER-290 could be dispersed in water with PC, and that the dispersibility was dependent on PC amounts.

Experiment Example 3

Formation of Microparticles with Additives

In order to reduce the particle size in S/W, the additives presented in Table 1 were added to the aqueous phase of the S/O/W emulsion during the preparation of S/W, and the dispersibility of each sample was observed.

(1) An ER-290-FITC-DEX complex solid was obtained by freeze drying the W/O emulsion prepared by agitating 3.0 mL of a 0.1 Tris-HCl.EDTA buffer (TE buffer: 1.0 mM Tris-HCl, 0.10 mM EDTA, pH 8.0; containing 100 µg/mL FITC-DEX (molecular weight of about 2,000,000; Sigma)), and 30 mL of a cyclohexane solution (containing 500 µg/mL ER-290) in a 50-mL eggplant flask using a homogenizer (26,000 rpm, 2 min).

(2) Cyclohexane (3.0 mL) was added to (1) to obtain an FITC-DEX-encapsulated S/O.

(3) A PC-ER-290-FITC-DEX complex solid was obtained by freeze drying the S/O/W emulsion prepared by agitating the solution of (2) (0.50 mL), and 5.0 mL of an aqueous solution (containing 2.5 mg/mL PC, and each additive at a concentration of 125 mg/mL) in a 12-mL vial container using a homogenizer.

(4) A 0.1 TE buffer (5.0 mL) was added to (3) to obtain an FITC-DEX-encapsulated S/W.

TABLE 1

| Type | Additive | Preparation concentration |
|---|---|---|
| Sugar alcohol | Glycerine, xylitol, sorbitol | 125 mg/mL |
| Monosaccharide | Glucose | |
| Disaccharide | Sucrose, trehalose | |
| Polysaccharide | Dextran (molecular weight: 15,000 or 200,000) | |

Figure 3:
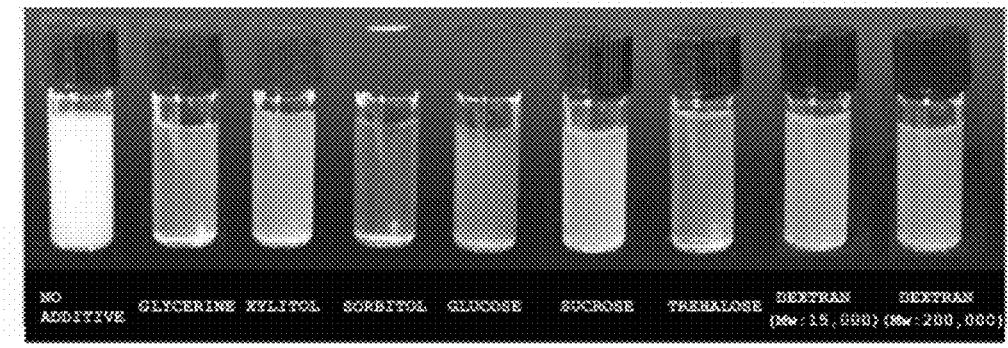
FIG. 3 is a photographic representation showing changes in dispersibility of FITC-DEX-encapsulated S/W.
Figure 4:
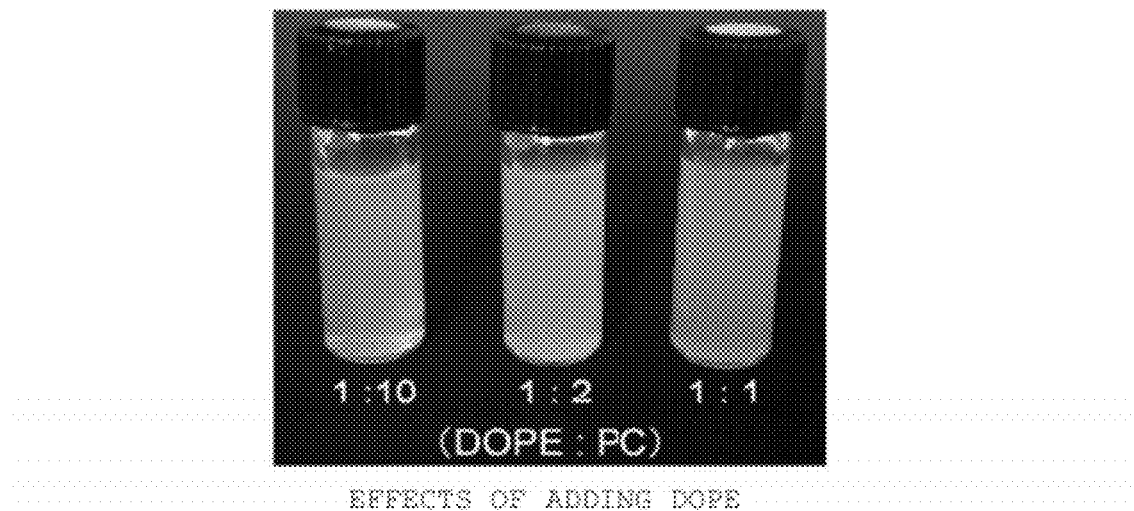
FIG. 4 is a photographic representation showing the effects of adding DOPE.

The results shown in FIG. 3 confirmed that the dispersibility improves with low-molecular sugars such as sugar alcohol and simple sugars added in equal weights. Glycerine, sorbitol, and trehalose, in particular, produced S/W of relatively small particle sizes.

Experiment Example 4

Effects of Adding DOPE

Use of S/W as a gene vector requires adding DOPE to the system for endosomal escape in the cells. However, because DOPE is a highly hydrophobic lipid, DOPE was added to the oily phase of the S/O/W emulsion during the preparation of S/W, in an effort to disperse DOPE in water with PC, together with the ER-290-drug complex. Assessments were made with FITC-DEX-encapsulated S/W at varying DOPE:PC weight ratios (1:10, 1:2, 1:1).

(1) An FITC-DEX-encapsulated S/O was obtained by adding 3.0 mL of cyclohexane (containing 5.0 or 25 mg/mL DOPE (dioleoyl phosphatidyl-ethanolamine; Avanti)) to (1) of Experiment Example 3.

(2) In order to obtain complexes in the compositions shown in Table 2, a PC-(DOPE)-ER-290-FITC-DEX complex solid was obtained by freeze drying the S/O/W emulsion prepared from 0.50 mL of the solution of (1), and 5.0 mL of an aqueous solution containing 2.5 or 5.0 mg/mL PC and 50 mg/mL sorbitol.

(3) A 0.1 TE buffer (5.0 mL) was added to (2) to obtain an FITC-DEX-encapsulated S/W.

TABLE 2

| FITC-DEX | ER-290 | DOPE | PC | DOPE:PC |
|---|---|---|---|---|
| 50 μg | 2.5 mg | 5.0 mg | 50 mg | 1:10 |
| | | 25 mg | 50 mg | 1:2 |
| | | 25 mg | 25 mg | 1:1 |

As can be seen from the results presented in FIG. 4, the particle size increased with increase in DOPE ratio with respect to PC. However, because there was no DOPE or ER-290 precipitation in any of the samples even after several days, it was confirmed that S/W that contains DOPE could be prepared in the compositions presented in Table 2.

Experiment Example 5

DNA-Encapsulated S/W Particle Size and Ease of Encapsulation

A pDNA-encapsulated S/W (10 μg/mL) was prepared at a DOPE:PC weight ratio of 1:1, and the particle size and ease of encapsulation were evaluated.

(1) An ER-290-pDNA complex solid was obtained by freeze drying the W/O emulsion prepared by agitating 0.50 mL of a 100 μg/mL pDNA-containing 0.1 TE buffer, and 5.0 mL of a 500 μg/mL ER-290-containing cyclohexane solution in a 12-mL vial container using a homogenizer.

(2) A pDNA-encapsulated S/O (containing DOPE) was prepared by adding 5.0 mL of a cyclohexane solution (containing 5.0 mg/mL DOPE) to (1). The sample was evaluated by dynamic light scattering (DLS) measurement and TEM observation after adding a cyclohexane solution (5.0 mL) to (1).

(3) A PC-(DOPE)-ER-290-pDNA complex solid was obtained by freeze drying the S/O/W emulsion prepared by agitating 0.50 mL of the solution obtained in (2), and 5.0 mL of an aqueous solution (containing 0.50 mg/mL PC and 50 mg/mL sorbitol) in a 12-mL vial container using a homogenizer.

(4) A 0.1 TE buffer (0.50 mL) was added to (3) to obtain a pDNA-encapsulated S/W.

(5) The particle size of the resulting S/W was evaluated by DLS measurement and TEM observation.

(6) The ease of encapsulation of the pDNA in the S/W was evaluated by 1.5% agarose gel electrophoresis (135 V, 30 min, ethidium bromide staining). Electrophoresis was also performed for samples in which 1% Triton X-100 was added as a solubilizer, and for samples (physical mixture) prepared at a zero pDNA concentration in (1), in which a 0.1 TE buffer containing 10 μg/mL pDNA was added in (4).

Figure 5:
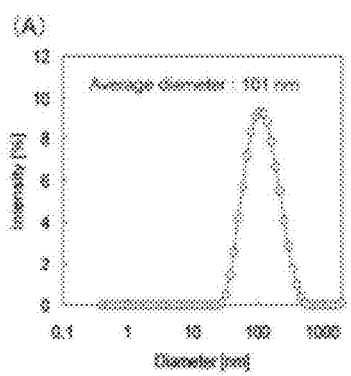
FIG. 5 represents property diagrams and electromicrographs concerning the pDNA-encapsulated S/O and S/W particle size.
Figure 5:
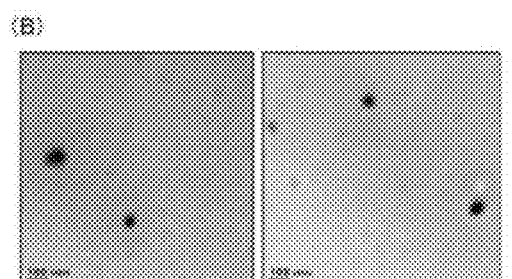
Figure 5:
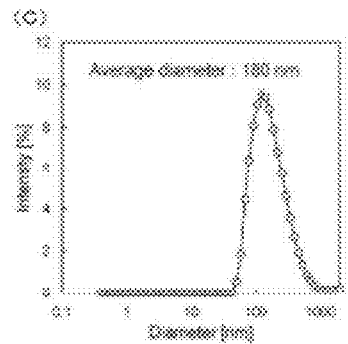
Figure 5:
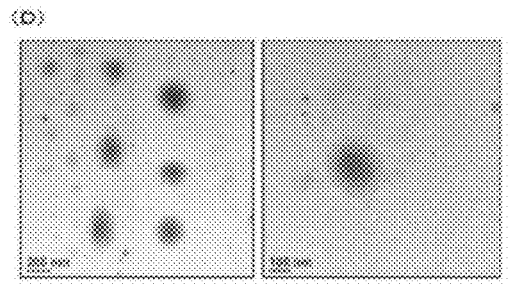

The results shown in FIG. 5 suggested that the S/O and S/W prepared under the foregoing conditions had particle sizes of about 100 nm and about 180 nm, respectively. The particle volumes approximated from these results were $5.2 \times 10^5$ nm$^3$ and $3.1 \times 10^6$ nm$^3$ for S/O and S/W, respectively, and the volume ratio was about 1:5.8. Specifically, calculations indicate that, on average, 5.8 ER-290-pDNA complexes exist in a single S/W particle. Here, because it is believed that the ER-290-pDNA complexes exist in large numbers in the oil droplets of the S/O/W emulsion during the preparation of the S/W, there is no surprise that a single S/W particle actually contains more than 5.8 ER-290-pDNA complexes. Further, because the results of both DLS measurement and TEM observation revealed that the S/W particle size distribution did not represent a monodispersion, the level of completion as a nanoparticle was considered low. In the MEND system using R8, however, cell delivery was confirmed possible even with the particle sizes of about 1.0 μm, and thus the foregoing particle size range was considered to be sufficient for use as a gene vector, even though the particle size distribution was wide.

Further, the S/W solution immediately after preparation was subjected to agarose gel electrophoresis to evaluate the ease of pDNA encapsulation. Electrophoresis was also performed for a sample in which all the components in the S/W were solubilized by addition of the strong non-ionic surfactant Triton X-100, and for a sample (physical mixture) in which a pDNA aqueous solution was added after preparing a blank S/W to mimic the 100% pDNA released state.

Figure 6:
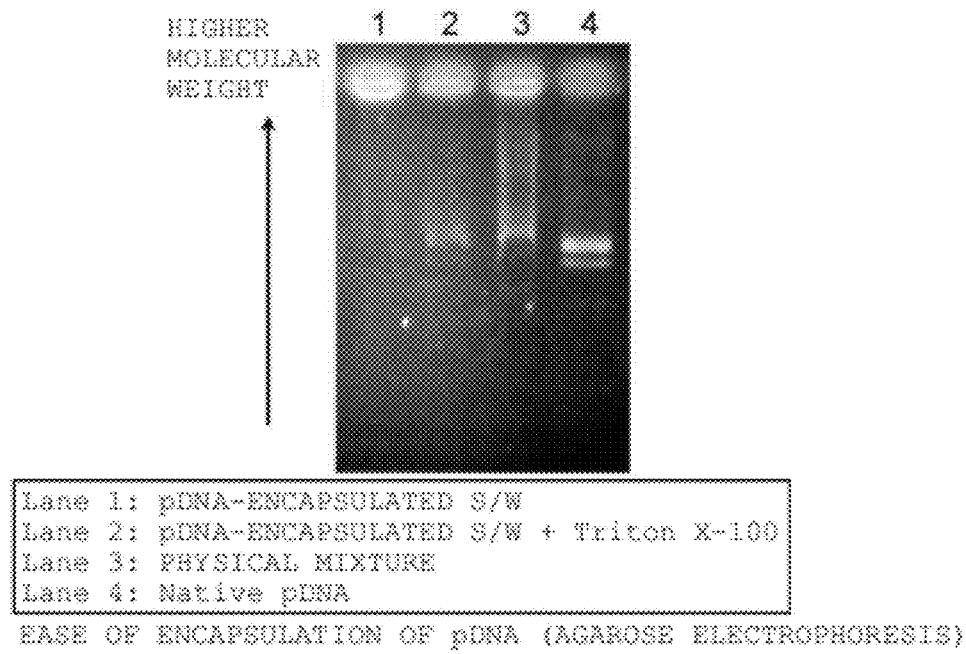
FIG. 6 is a photographic representation of agarose electrophoresis concerning the ease of encapsulation of pDNA.

Lane 1 in FIG. 6 shows the agarose electrophoresis result for the pDNA-encapsulated S/W. As can be seen in FIG. 6, there is no pDNA band (as seen in Lane 4), and a pDNA band occurs when all the components in S/W are solubilized (S/W disruption; Lane 2), and further the electrophoresis result in Lane 1 differs from the result of the sample in which DNA was added after preparing a blank S/W (Lane 3). These results suggested that the pDNA formed a complex with the surfactant in S/W, and did not run farther from the cast portion of the gel. These results are supportive of the pDNA being encapsulated inside the S/W complex, and demonstrate that the DNA was successfully encapsulated in the carrier without a highly cationic substance.

Experiment Example 6

Use for Gene Vector

A pDNA-encapsulated S/W modified with R8-str (stearyl octaarginine) was prepared in varying DOPE:PC weight ratios (1:10, 1:2, 1:1), and evaluated for luciferase expressibility against B16 cells under the conditions below. Assessments were also made for control samples that did not contain DOPE and/or R8-str (Table 3), and for Lipofectamine, based on the DOPE:PC weight ratio of 1:1.

(1) An ER-290-pDNA complex solid was obtained by freeze drying the W/O emulsion prepared by agitating 0.50 mL of a 100 μg/mL pDNA-containing 0.1 TE buffer and 5.0 mL of a 500 μg/mL ER-290-containing cyclohexane solution in a 12-mL vial container using a homogenizer.

(2) A pDNA-encapsulated S/O (containing DOPE) was prepared by adding 5.0 mL of a cyclohexane solution (containing 0.50, 2.5, 5.0 mg/mL DOPE) to (1).

(3) In order to prepare complexes in the compositions shown in Table 3, a PC-(DOPE)-ER-290-pDNA complex solid was obtained by freeze drying the S/O/W emulsion prepared by agitating the solution (0.50 mL) of (2), and 5.0 mL of an aqueous solution (containing 0.50 mg/mL PC, 0.11, 0.15, 0.20 mg/mL R8-str, and 30, 40, 50 mg/mL sorbitol) in a 12-mL vial container using a homogenizer.

(4) The control samples presented in Table 3 were prepared by appropriately making the pDNA, DOPE, and R8-str concentrations zero in (1) to (3).

(5) The B16 cells cultured in D-MEM medium were counted, and cultured overnight after being inoculated in a 24-well plate and a 96-well plate ($5 \times 10^3$ cells/well).

(6) Reduced serum medium (Opti-MEM Invitrogen) was added to the solids obtained in (3) and (4), and the cells were cultured for 3 hours after being inoculated on the plates (5) at a pDNA concentration of 1.0 μg/well.

Gene expression analysis was also conducted with Lipofectamine (Lipofectamine 2000; Invitorogen) using the same quantity of pDNA. Here, wells with only Opti-MEM (controls and blanks) were also prepared in the 96-well plate.

(7) The medium was removed from the 96-well plate after 3 hours from (6), and a WST-8 solution (containing 1-methoxy-PMS) was added to perform a color reaction for 2 hours. Absorbance at 450 nm was measured, and cell viability was determined relative to the control using the foregoing formula 1.

(8) The medium was removed from the 24-well plate after 3 hours from (6), and the cells were cultured after adding D-MEM medium.

(9) The medium was removed after 2 days from (7), and the cells were centrifuged after adding a cell lysate (lysis buffer: 20 mM Tris-HCl, 2 mM EDTA, 0.05% TritonX-100, pH 7.5). Luciferase activity was then measured after adding luciferin. The protein concentration in the cell lysate was measured using the Bradford technique, and normalized.

(10) For samples (c) and (g), a 0.1 TE buffer (5.0 mL) was added after the preparation of the PC-(DOPE)-ER-290-pDNA complex in (3), and the zeta potential was measured.

Finally, the luciferase expressibility of the pDNA-encapsulated S/W modified with R8-str and prepared at a DOPE:PC weight ratio of 1:10, 1:2, or 1:1 was confirmed by experimentation. Assessments were also made for the control samples that did not contain the components presented in Table 3, and for Lipofectamine, based on the DOPE:PC weight ratio of 1:1. Zeta potential measurements were performed for the samples (c) and (g) in Table 3.

Figure 7:
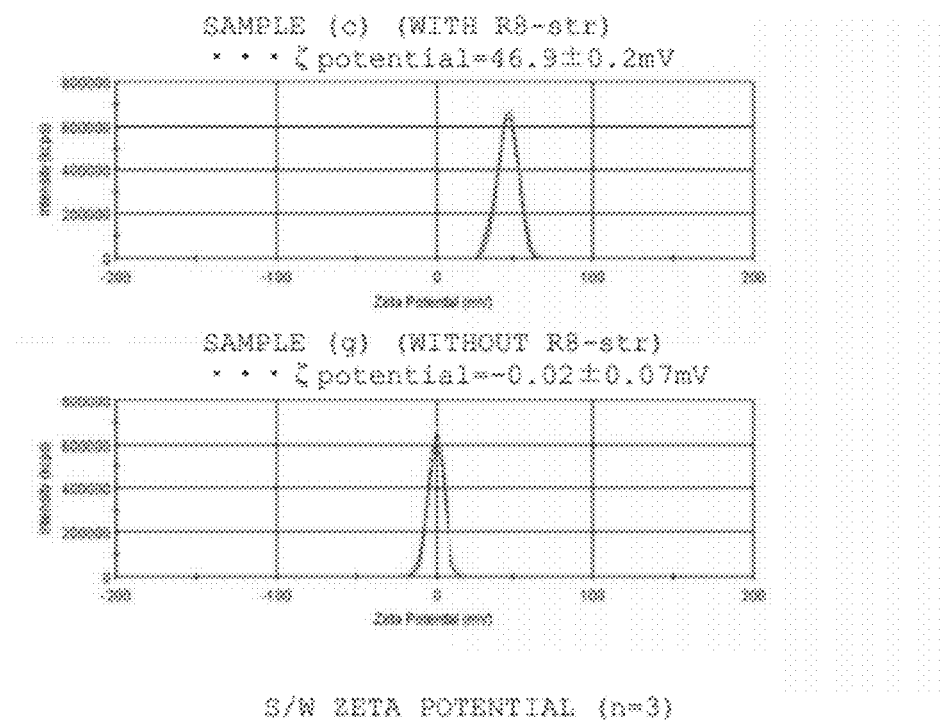
FIG. 7 is a graph concerning S/W zeta potential.

FIG. 7 presents the results of the zeta potential measurements for samples (c) and (g). The results showed that the R8-str created a cationic charge on the particle surface, confirming that the S/W surface was modified with the octaarginine. The D-MEM medium typically used for animal cell cultures contains fetal bovine serum, and the S/W having the cationic surface has the risk of forming an aggregate with the albumin contained in the serum. To avoid this, the gene expression experiment was conducted in a serum reduced medium (Opti-MEM). Because the cells cannot be cultured any longer than half a day in Opti-MEM, the medium was exchanged to D-MEM medium after 3 hours from the sample administration.

TABLE 3

| No. | pDNA | ER-290 | DOPE | PC | R8-str | Sorbitol |
|-----|------|--------|------|------|--------|----------|
| (a) | 5.0 μg |  | 0.25 mg |  | 0.55 mg | 150 mg |
| (b) | 5.0 μg |  | 1.25 mg |  | 0.75 mg | 200 mg |
| (c) | 5.0 μg |  | 2.5 mg |  | 1.0 mg | 250 mg |
| (d) | 5.0 μg* |  | 2.5 mg |  | 1.0 mg | 250 mg |
| (e) | 5.0 μg | 250 μg | 2.5 mg | 2.5 mg | 1.0 mg* | 250 mg |
| (f) | 5.0 μg |  | — |  | 1.0 mg | 250 mg |
| (g) | 5.0 μg |  | 2.5 mg |  | — | 250 mg |
| (h) | 5.0 μg |  | — |  | — | 250 mg |

Figure 8:
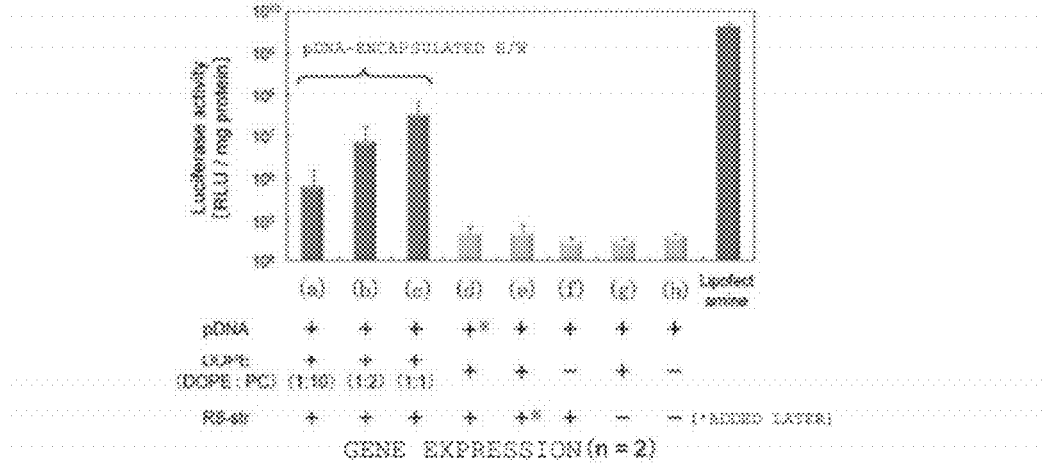
FIG. 8 is a graph representing gene expression (n=2).

As can be seen from the results presented in FIG. 8, luciferase expression occurred in the pDNA-encapsulated S/W and in Lipofectamine, not in the control samples. This suggests that gene expression does not occur unless the necessary elements for expression, including pDNA, DOPE, and R8-str, properly combine in the S/W. Further, gene expression by the R8-str-induced endocytosis or by the DOPE proton sponge effect was confirmed from the increased luciferase expression levels with increased amounts of DOPE and R8-str added in the pDNA-encapsulated S/W, and from the expression failure with the R8-str (f) or DOPE (g) alone.

Figure 9:
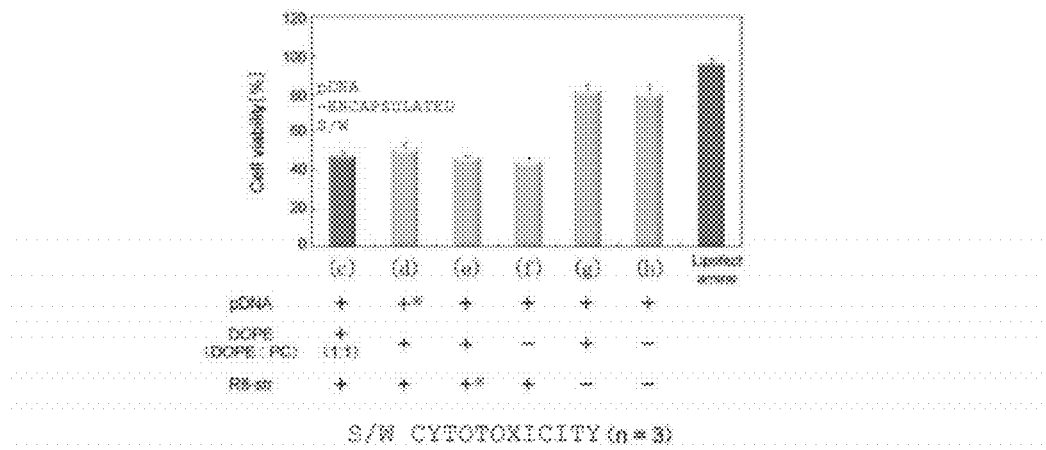
FIG. 9 is a graph representing S/W cytotoxicity (n=3).

FIG. 9 shows the results of cell viability measurements after 3 hours from the sample administration. Here, viability was calculated relative to the 100% cell viability in a 3-hour culture with Opti-MEM. While there was almost no cytotoxicity in the samples themselves in samples (g) and (h) (containing no octaarginine) and in Lipofectamine, the cell viability was about 40% in samples (c) to (f) that contained octaarginine.

Figure 10:
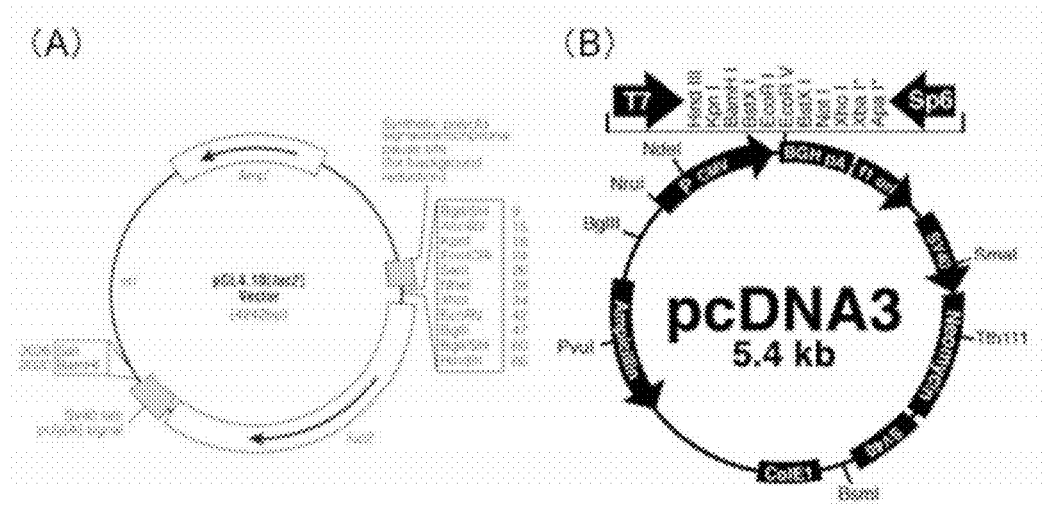
FIG. 10 is a diagram representing gene information.
Figure 11:
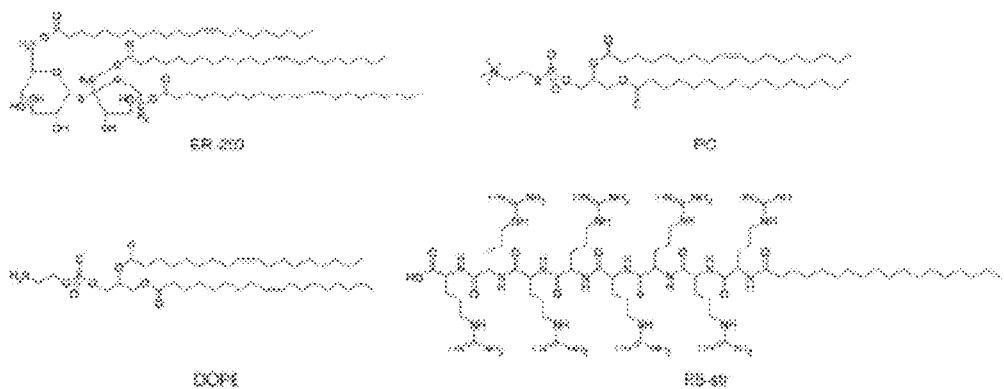
FIG. 11 is a diagram representing surfactant structural formulae.

The model plasmid DNA (pDNA) used in the foregoing Experiment Examples is a pDNA of about 7.4 kbp (molecular weight: 3,000,000 to 4,000,000) that expresses luciferase in an animal cell. The pDNA was recombined, extracted, and purified at Invitrogen, based on a gene obtained by inserting the luc2 gene (FIG. 10A) into the restriction enzyme site shown in FIG. 10B. The ER-290 is a mixture of a diester and a triester of sucrose and erucic acid (22:1), and the PC is a mixture of saturated hydrocarbon and unsaturated hydrocarbon having 12 to 22 carbon atoms on the alkyl chain. The structural formulae are shown in FIG. 11 along with DOPE and R8-str.

Experiment Example 7

Cytotoxicity of PEG-Modified Surfactants (1) B16 cells were cultured overnight after being inoculated in a 96-well plate ($5 \times 10^3$ cells/well).

(2) The solution was removed from (1), and the cells were cultured for 1 day after adding PC, PEG(2K)-MS, PEG(2K)-DSPE, PEG(5K)-DSPE, and PEG(comb)-DSPE (100 mL each) of varying concentrations prepared in serum medium. Wells containing only the serum medium were also prepared as controls or blanks. Note that the "serum medium" as used herein refers to D-MEM that contains 10% FBS and antibiotics (both available from Invitorogen).

(3) The solution was removed from (2), and a serum medium solution containing 2-(2-methoxy-4-nitrophenyl)-3-(4-nitrophenyl)-5-(2,4-disulfo-phenyl)-2H-tetrazolium (WST-8) and 1-methoxy-5-methyl-phenazinium methylsulfate (1-methoxy-PMS) (attached to the Cell Counting Kit-8) was added to perform a color reaction for 4 hours. Absorbance at 450 nm was measured, and cell viability was determined relative to the control using the formula 1.

Figure 12:
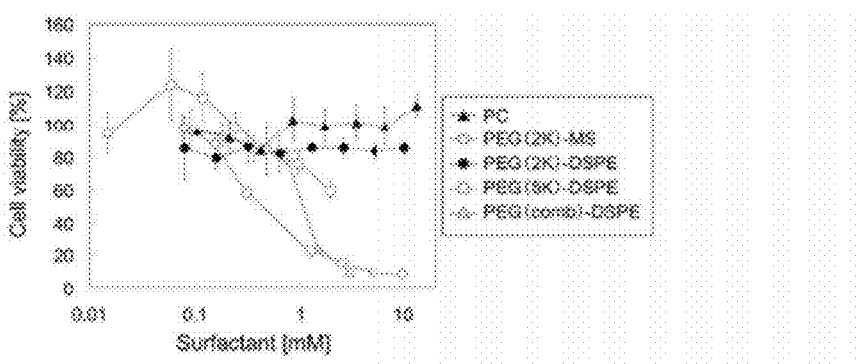
FIG. 12 is a graph representing the cell activity of PEG-modified genes.

It was found from the results presented in FIG. 12 that the PEG(2K)-DSPE and PC were almost non-toxic at any concentration. The results revealed that the PEG(2K)-DSPE and PC were surfactants having potential to improve the ease of encapsulation into a carrier, and that the other surfactants were also non-toxic below certain concentrations.

Experiment Example 8

PEG-Modified Surfactant Cytotoxicity and Gene Expression (1) An ER-290-pDNA complex solid was obtained by freeze drying the W/O emulsion prepared by agitating 0.5 mL of a 50 μg/mL pDNA-containing 0.1×Tris-HCl EDTA buffer (TE buffer: 10 mM Tris-HCl, 1 mM EDTA, pH 8.0), and 5.0 mL of a 0.5 mg/mL ER-290-containing cyclohexane solution.

(2) A pDNA-encapsulated S/O (containing DOPE) was prepared by adding 2.5 mL of a cyclohexane solution (containing 4.5 mg/mL (6.0 mM) DOPE) to (1).

(3) A total of five surfactant-(DOPE)-ER-290-pDNA complex solids presented in Table 4 were obtained by freeze drying the S/O/W emulsion prepared by agitating the solution (0.50 mL) of (2), and 5.0 mL of aqueous solutions that contained 0.9 mg/mL (1.2 mM) PC, 2.4 mg/mL (1.2 mM) PEG(2K)-MS, 3.6 mg/mL (1.2 mM) PEG(2K)-DSPE, 7.2 mg/mL (1.2 mM) PEG(5K)-DSPE, and 28.8 mg/mL (1.2 mM) PEG(comb)-DSPE.

(4) A serum medium (5.0 mL) was added to (3) to obtain a total of five 1.0 mg/mL pDNA-containing S/W samples presented in Table 4.

(5) Cells were cultured overnight after being inoculated in a 24-well plate ($5 \times 10^4$ cells/well), and 1.0 mL of the serum medium solution of (1) was added (pDNA 1.0 μg/well). Here, a pDNA-containing serum medium solution (naked pDNA), a naked pDNA plus an appropriate amount of Lipofectamine (N/P =1.5), and a pDNA-containing serum reduced medium (Opti-MEM) plus an appropriate amount of Lipofectamine (N/P =1.5) were used as controls.

(6) The wells that had Opti-MEM were exchanged to serum medium after 3 hours from (5).

(7) The medium was removed after 1 day from (5), and the cells were washed with Dulbecco's phosphate buffered saline (D-PBS), and lysed by adding a 0.05% Triton X-100-containing TE buffer. After centrifugation, luciferin was added to the supernatant, and luciferase emission (relative light unit, RLU) was measured. The protein concentration in the supernatant was measured by using the Bradford technique, and normalized.

(8) Cells were cultured overnight after being inoculated in a 96-well plate ($5 \times 10^3$ cells/well), treated by the same procedures performed in (5) to (6), and evaluated for cytotoxicity by the same procedures performed in Experiment Example 7, using the serum medium solution as a control and a blank. Note that the PEG-modified surfactants are all NOF Corporation products.

TABLE 4

| No. | (a) | (b) | (c) | (d) | (e) |
|-----|-----|-----|-----|-----|-----|
| pDNA |  |  | 1.0 μg |  |  |
| ER-290 |  |  | 100 μg |  |  |
| DOPE |  |  | 0.45 mg |  |  |
| PC | 0.9 mg | — | — | — | — |
| PEG(2K)-MS | — | 2.4 mg | — | — | — |
| PEG(2K)-DSPE | — | — | 3.6 mg | — | — |
| PEG(5K)-DSPE | — | — | — | 7.2 mg | — |
| PEG(comb)-DSPE | — | — | — | — | 28.8 mg |

Figure 13:
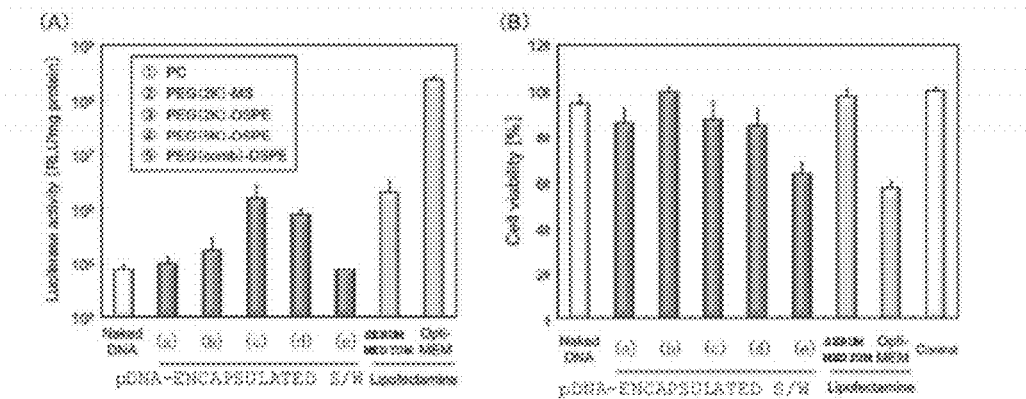
FIG. 13 shows graphs representing the cytotoxicity and gene expressibility of pDNA-encapsulated S/W.

Gene expression efficiency 24 hours after the addition of the B16 cells was evaluated by luciferase assay using carriers prepared to include surfactants and DOPE. The surfactants were contained at a concentration of 1.2 mM, at which the cytotoxicity of all the surfactants was found to disappear from the results of Experiment Example 7, and the DOPE was added at a concentration of 0.6 mM. FIG. 13(A) shows the gene expression results, and FIG. 13(B) the cytotoxicity results. Gene expression was observed in S/W samples prepared with PEG(2K)-DSPE and PEG(5K)-DSPE, and there was almost no cytotoxicity in these samples. In the observed cells, particle aggregation was clearly visible in PC and PEG (2K)-MS, and the absence of gene expression was considered to be due to the precipitation caused by the serum. Further, the gene expression effect was notably smaller than in the sample in which Lipofectamine was used in Opti-MEM. However, the carriers prepared in this Experiment Example had better results in cytotoxicity, confirming that the carriers may be effective for expression in cells weaker than B16 cells.

Figure 14:
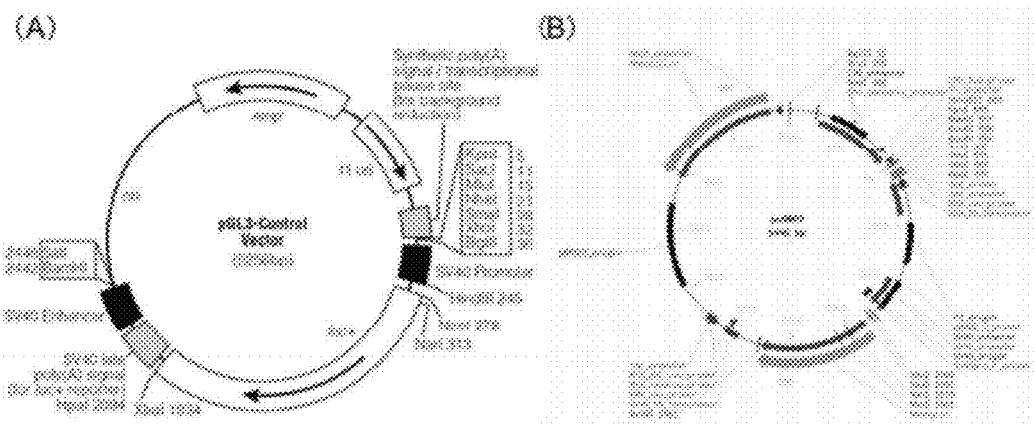
FIG. 14 is a diagram representing gene information.

The pDNA used in Experiment Example 8 is one obtained by inserting the luc+ gene (FIG. 14(A)) into the Hind III to Xba I site of FIG. 14(B), and was used after the extraction and purification of cultured *Escherichia coli* with the pDNA of this sequence being transformed at Mitsuwa Frontec Corp.

Figure 15:
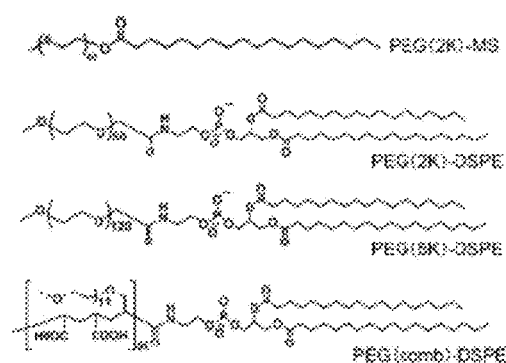
FIG. 15 is a diagram representing surfactant structural formulae.

FIG. 15 shows the structural formulae of PEG(2K)-MS, and three kinds of PEG-DSPE (the stearic acid has 18 carbon atoms) derivatives. These three PEG-DSPE derivatives are simply denoted as PEG(2K)-DSPE, EG(5K)-DSPE, PEG (comb)-DSPE.

Experiment Example 9

Ease of Encapsulation in PEG(2K)DSPE-Modified S/W and Gene Expression (1) An ER-290-pDNA complex solid was obtained by freeze drying the W/O emulsion prepared by agitating 2.0 mL of a 20 μg/mL pDNA-containing Buffer #1 (0.25 mM Tris-HCl, 0.025 mM EDTA, pH 8.0), and 4.0 mL of a cyclohexane solution that contained ER-290 (1.1 mg/mL).

(2) A cyclohexane solution (2.0 mL) containing DOPE (7.5, 15 mg/mL (10, 20 mM)) was added to (1) to prepare a pDNA-encapsulated S/O (containing DOPE).

(3) A total of nine surfactant-(DOPE)-ER-290-pDNA complex solids presented in Table 5 were obtained by freeze drying the S/O/W emulsion prepared by agitating the solution (0.50 mL) of (2), and an aqueous solution (5.0 mL) obtained by combining PC (0.75, 1.5 mg/mL (1.0, 2.0 mM)) and PEG (2K)DSPE (3.0, 6.0, 12 mg/mL (1.0, 2.0, 4.0 mM)).

(4) Serum medium (5.0 mL) was added to (3) to obtain the nine S/W samples containing 2.0 mg/mL pDNA (Table 5).

(5) Milli Q water (5.0 mL) was added to (3), and the ease of encapsulation of the pDNA in the S/W was evaluated by agarose gel electrophoresis. Electrophoresis was also performed for a sample in which the carrier was disrupted by 1% Triton X-100.

(6) B16 cells were cultured overnight after being inoculated in a 24-well plate ($5 \times 10^4$ cells/well), and the serum medium solution of (4) was added in 0.5 mL/well (pDNA 1.0 μg/well). A sample obtained by adding an appropriate amount of Lipofectamine (N/P=1.5) to the pDNA-containing serum medium solution was used as a control.

(7) The medium was removed after 1 day from (6), and the cells were washed with Dulbecco's phosphate buffered saline (D-PBS), and lysed by adding 0.05% Triton X-100-containing TE buffer. After centrifugation, luciferin was added to the supernatant, and luciferase emission (relative light unit, RLU) was measured. The protein concentration in the supernatant was measured by using the Bradford technique, and normalized.

(8) B16 cells were cultured overnight after being inoculated in a 96-well plate ($5 \times 10^3$ cells/well), and the serum medium solution of (4) was added in 100 μL/well. Here, wells containing only the serum medium were also prepared as controls or blanks.

(9) The solution was removed after 1 day from (8), and a serum medium solution containing 2-(2-methoxy-4-nitrophenyl)-3-(4-nitrophenyl)-5-(2,4-disulfo-phenyl)-2H-tetrazolium (WST-8) and 1-methoxy-5-methyl-phenazinium methylsulfate (1-methoxy-PMS) (attached to the Cell Counting Kit-8) was added to perform a color reaction for 2 hours. Absorbance at 450 nm was measured, and cell viability was determined relative to the control using the formula 1.

TABLE 5

| No. | (a) | (b) | (c) | (d) | (e) | (f) | (g) | (h) | (i) |
|---|---|---|---|---|---|---|---|---|---|
| pDNA [μg/mL] | | | | | 2.0 | | | | |
| ER-290 [mM] | | | | | 0.2 | | | | |
| DOPE [mM] | 1.0 | 1.0 | 1.0 | 1.0 | 1.0 | 2.0 | 2.0 | 2.0 | 2.0 |
| PC [mM] | 1.0 | — | 1.0 | — | 2.0 | — | 2.0 | — | 2.0 |
| PEG(2K)DSPE [mM] | — | 1.0 | 1.0 | 2.0 | 2.0 | 2.0 | 2.0 | 4.0 | 4.0 |

Figure 16:
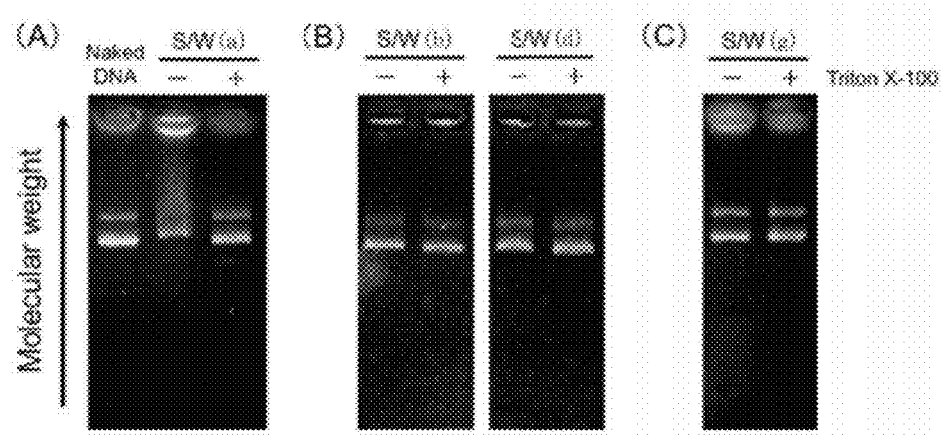
FIG. 16 is a photographic representation of agarose gel electrophoresis.

From the indication that PEG(2K)DSPE is suited as the S/W outer surfactant, the ease of encapsulation of the pDNA into the carrier was evaluated by agarose gel electrophoresis. The ease of encapsulation of the pDNA was evaluated by performing electrophoresis for samples (b) and (d) (DOPE:PEG(2K)DSPE=1:1, 1:2) in Table 5. It was reasoned that encapsulation of the pDNA in the carrier would create a band on the higher molecular weight side compared to the Naked DNA. Simultaneously, pDNA collectability was also evaluated by disrupting the carrier with the strong non-ionic surfactant Triton X-100. FIG. 16 shows the results. It was found from the results presented in FIG. 16(B) that the S/W prepared with PEG(2K)DSPE hardly encapsulated the pDNA. PEG(2K)DSPE was thought to be almost non-toxic to the B16 cells and have low solubilizing power. However, the agarose gel electrophoresis result showed that there was almost no difference in the band position from the sample in which Triton X-100 was added. FIG. 16(A) shows the electrophoresis result for sample (a) prepared by using the same number of moles as in (b) for the surfactant PC. In the result, the pDNA had leakage, and was observed also at the cast portion of the gel, and thus the electrophoresis result was different from that obtained after disruption with Triton X-100. It can therefore be seen that the type of surfactant has a large effect on the ease of encapsulation into the carrier. As support, slight pDNA encapsulation was confirmed in the S/W sample (g) that used PC and PEG(2K)DSPE in combination, as shown in FIG. 16(C). The improved ease of encapsulation may improve gene expression efficiency, but with possible simultaneous aggregation with PC.

Figure 17:
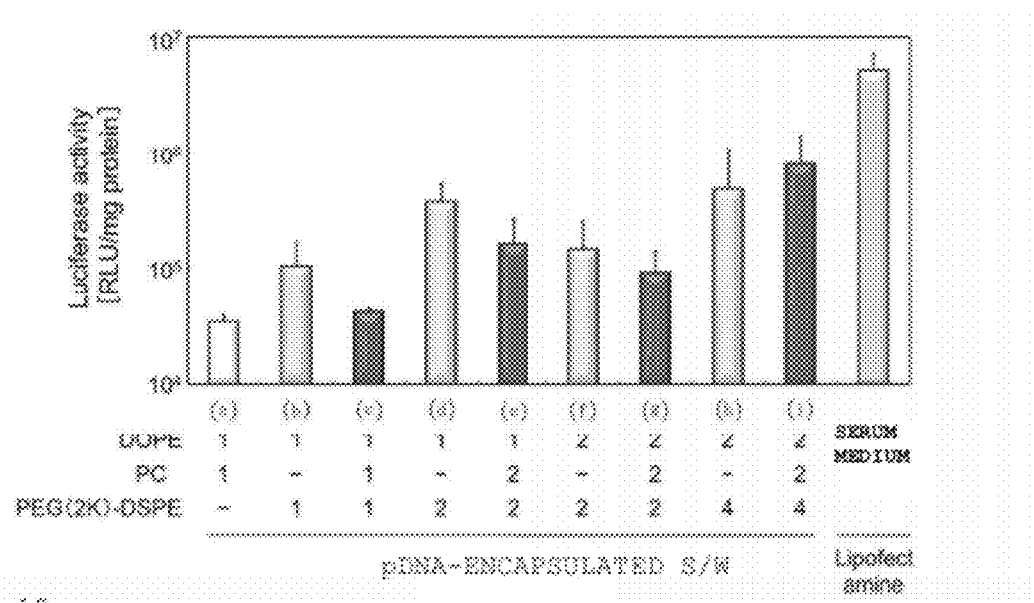
FIG. 17 is a graph representing the gene expressibility of pDNA-encapsulated S/W.

Gene expression experiment and cytotoxicity experiment were performed for the all samples in Table 5. Cell viability was 70 to 96%, and there was almost no cytotoxicity in the all samples. FIG. 17 shows the gene expression results. There was no gene expression in sample (a) prepared by using only PC for the outer surfactant. Particle aggregation occurred in the observed cells. Gene expression was confirmed in samples (b), (d), (f), and (h) (DOPE:PEG(2K)DSPE=1:1, 1:2, 2:2, 2:4) prepared by using only PEG(2K)DSPE for the outer surfactant, and the particle aggregation was clearly less than that observed in sample (f). However, there was no increase in the DOPE-induced gene expression. Further, the samples (c), (e), (g), and (i) (DOPE:PC:PEG(2K)DSPE=1:1:1, 1:2:2, 2:2:2, 2:2:4) prepared with the expectation to improve the ease of encapsulation of the pDNA by PC had clearly less particle aggregation than sample (a) in the observed cells. This suggests that the particle aggregation by PC was suppressed by the coating of the particle surface with PEG. However, in terms of gene expression, these samples did not differ greatly from samples (b), (d), (f), and (h) that used only PEG(2K)DSPE.

Experiment Example 10

Ease of Encapsulation in PEI-Added S/W and Gene Expression (1) PEI was dissolved in 1 M HCl at a concentration of 10 mg/mL, and an appropriate amount of 1 M Tris-HCl (pH 9.0) was added to the solution to adjust pH. Then, an appropriate amount of TE buffer (10 mM Tris-HCl, 1.0 mM EDTA, pH 8.0) was added to prepare a 10×PEI(1.07 mM PEI, 250 mM Tris-HCl, 0.25 mM EDTA, pH 6.0) used to finally make a PEI-pDNA complex solution (2.0 mL) that contains 20 μg/mL pDNA (N/P=10).

(2) An ER-290-pDNA complex solid was obtained by freeze drying the W/O emulsion prepared by agitating 2.0 mL of Buffer #2 (25 mM Tris-HCl, 0.025 mM EDTA, pH 6.0; containing 20 μg/mL pDNA and 0.107 mM PEI), and 4.0 mL of a cyclohexane solution that contained ER-290 (5.5, 11 mg/mL).

(3) A cyclohexane solution (2.0 mL) containing 3.75, 7.5, 15 mg/mL (5, 10, 20 mM) DOPE was added to (2) to prepare a pDNA-encapsulated S/O (containing DOPE).

(4) A total of four PEG(2K)DSPE-(DOPE)-ER-290-pDNA complex solids presented in Table 6 were obtained by freeze drying the S/O/W emulsion prepared by agitating the solution (0.50 mL) of (3) and an aqueous solution (5.0 mL) obtained by combining PEG(2K)DSPE (12, 24 mg/mL (4.0, 8.0 mM)).

(5) Serum medium (5.0 mL) was added to (4) to prepare a S/W sample containing 2.0 μg/mL pDNA, and gene expression experiment and cytotoxicity experiment were performed according to the methods used in 3.2.

(6) Milli Q water (5.0 mL) was added to (4), and the ease of encapsulation of the pDNA in the S/W was evaluated by agarose gel electrophoresis. Electrophoresis was also performed for a sample in which the carrier was disrupted by 1% Triton X-100, and for a sample in which the PEI was detached by PVSK.

TABLE 6

| No. | (j) | (k) | (l) | (m) |
|---|---|---|---|---|
| pDNA [μg/mL] | | | 2.0 | |
| ER-290 [mM] | 1.0 | 1.0 | 2.0 | 2.0 |
| DOPE [mM] | 0.5 | 1.0 | 2.0 | 2.0 |
| PEG(2K)DSPE [mM] | 4.0 | 4.0 | 4.0 | 8.0 |

For S/W gene expression in serum medium, it is considered necessary to decide optimum preparation conditions, taking into account (1) carrier particle size, (2) ease of encapsulation, (3) ease of sustained release, (4) (5) addition amounts of DOPE, (6) serum resistance, and (7) cytotoxicity. The poor ease of encapsulation into the carrier was considered to be the foremost reason for the limited gene expression efficiency in S/W using PEG(2K)DSPE. Thus, by reasoning that electrostatic repulsion of DNA may be involved in the pDNA leakage, the effect of pDNA aggregation on ease of encapsulation was investigated by addition of polycations. In this Experiment Example, linear polyethyleneimine (PEI), a polycation known to have the highest gene expression efficiency, was used.

Figure 18:
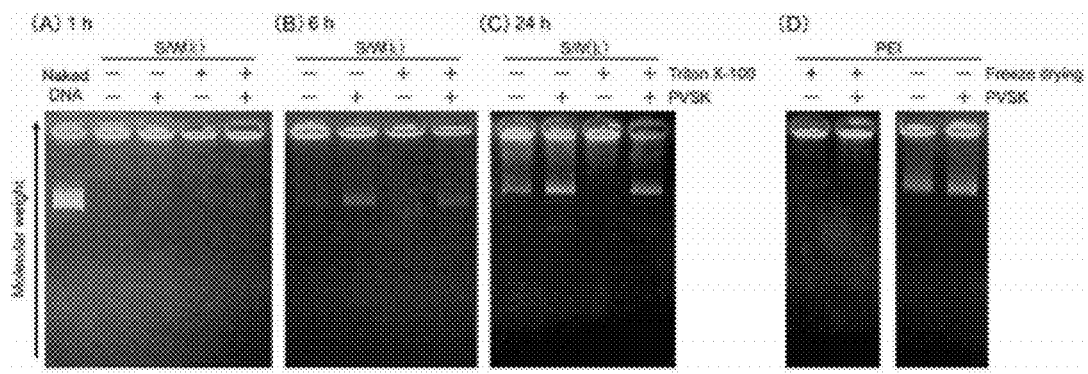
FIG. 18 is a photographic representation of electrophoresis.

FIG. 18 shows the results of agarose electrophoresis for S/W (k) samples after 1, 6, and 24 hours, and for the PEI-pDNA complex prepared as a mixture of PEI and pDNA (N/P=10). When electrophoresed as a complex with PEI, pDNA produces a band more toward the higher molecular weight side. To avoid this, the polyanion PVSK was used to detach the PEI from the PEI-pDNA complex. The PEI concentration was N/P=10 for all samples. As used herein, the N/P ratio is the ratio of (number of N atoms in PEI)/(number of P atoms in pDNA). Greater N/P ratios shift the pDNA electrophoresis result more toward the higher molecular weight side. In the calculation of the N/P ratio, the number of N atoms was taken as one for each PEI monomer (molecular weight of 43), and the number of P atoms as two for each pDNA monomer (a 1-bp A, T, G, C nucleotide with an average molecular weight of 640). From the electrophoresis result of the PEI-pDNA complex in FIG. 18(D) (N/P=10), it was found that the PEI-pDNA complex, at this N/P ratio, did not produce electrophoresis results that differed greatly from the result for the naked pDNA. Upon two runs of freeze drying, the band no longer moved from the cast portion of the gel, and no pDNA band occurred even with addition of PVSK. Though details remain unknown, it was found that the freeze drying procedure had a large effect on the state of at least the PEI-pDNA complex. In the agarose electrophoresis results for the S/W samples in FIGS. 18(A) to (C), a pDNA band occurs almost at the same position as in the naked pDNA as the standing time is made longer from 1 hour to 24 hours, particularly when PVSK is added. It can also be seen that the pDNA band appears gradually over the course of electrophoresis with S/W alone. Knowing that the PEI-pDNA complex hardly undergoes a high-molecular-weight shift at the N/P ratio used in this experiment, and by assuming that the pDNA band that occurred in samples with S/W alone after 24 hours is a PEI-pDNA complex band, there is a high possibility that the PEI-pDNA complex gradually leaked out of the S/W. Further, because a pDNA band occurred with PVSK, this result is considered to be different from the state produced by the PEI-pDNA complex that underwent two runs of freeze drying, and the effect on gene expression is expected to be small. The same results were also confirmed in S/W samples (j), (l), and (m) that contained other PEIs.

Figure 19:
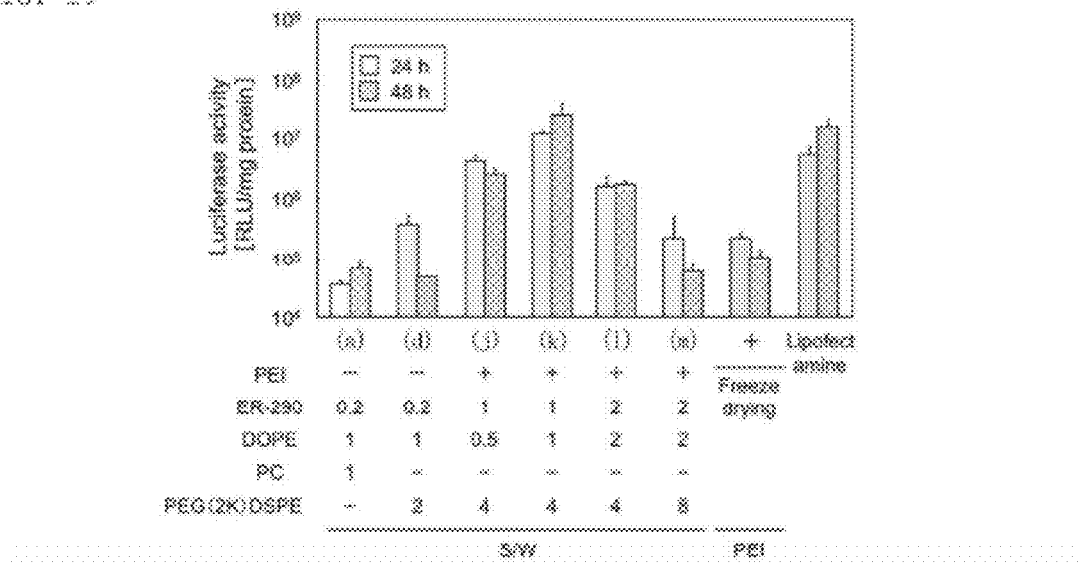
FIG. 19 is a graph representing the gene expressibility of PEI-added S/W.

FIG. 19 shows the results of gene expression experiment. As can be seen in FIG. 19, the highest gene expression efficiency ($2.8 \times 10^7$ [RLU/mg protein] after 48 hours) to date was achieved in S/W (k) (ER-290:DOPE:PEG(2K)DSPE=1:1:4). This expression efficiency is comparable to that obtained with Lipofectamine 2000 in D-MEM. Further, cell viability was 70 to 100%, and there was no notable toxicity in all samples, suggesting that the present technique has potential in constructing a new gene expression system. Leakage occurred immediately after the preparation in sample (d) prepared from the same surfactants (including PEG(2K)DSPE) but without adding PEI, and thus the gene expression efficiency always lowered to the background level after 48 hours. However, continuous gene expression was confirmed even at hour 48.

Figure 20:
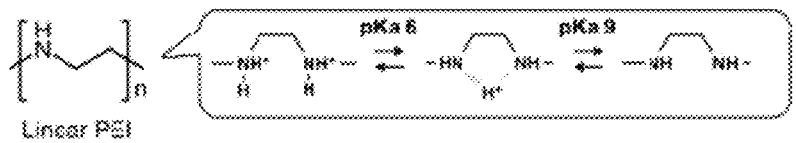
FIG. 20 is a diagram representing the structural formula of PEI.

The same pDNA used in Experiment Example 8 was used. FIG. 20 shows the structural formula of the PEI used in the experiments.

Experiment Example 11

Evaluation of Green Fluorescence Protein (EGFP) Introducibility into Cell

A green fluorescence protein (EGFP) with a molecular weight of about 27 kDa was used to prepare a S/W as an encapsulated protein drug model, and its introducibility into a cell was evaluated.

(1) A W/0 emulsion was adjusted by adding 2.0 mL of an EGFP aqueous solution (20, 60, 100, 200, 300 μg/ml; corresponding to (a) to (e) in Table 7) to a 1.1 mg/ml ER-290 cyclohexane solution (4.0 ml), and by agitating the mixture at high speed with a homogenizer (26,000 rpm, 2 min).

(2) The resulting solution was freeze dried to prepare an ER-290-EGFP complex (S/O complex). Cyclohexane (1.5 ml) was then added to the complex to adjust an EGFP-containing S/O.

(3) The resulting solution (0.375 ml) and a 60 mg/ml DOPE cyclohexane solution (0.125 ml) were added to a 1.5 mg/ml PC aqueous solution (5 ml) containing 1.2 mg/ml R4-str and 36.4 mg/ml sorbitol (SOR, stabilizer 10 for freeze drying), and the mixture was agitated at high speed with a homogenizer (22,000 rpm, 2 min) to prepare a S/O/W emulsion.

(4) The resulting solution was freeze dried to produce an EGFP-containing S/W complex, and 5 mL of Milli-Q water (experiment 1) or reduced serum medium (Opti-MEM; experiments 2, 3) was added to the solution to prepare an EGFP-containing S/W. Diluted sample solutions (2×, 4×) were also prepared.

TABLE 7

|   | EGFP | ER-290 | Composition ratio (g:g) |
|---|---|---|---|
| (a) | 40 μg | 4.4 mg | 1:110 |
| (b) | 120 μg |  | 1:37 |
| (c) | 200 μg |  | 1:22 |
| (d) | 400 μg |  | 1:11 |
| (e) | 600 μg |  | 1:7 |

Figure 21:
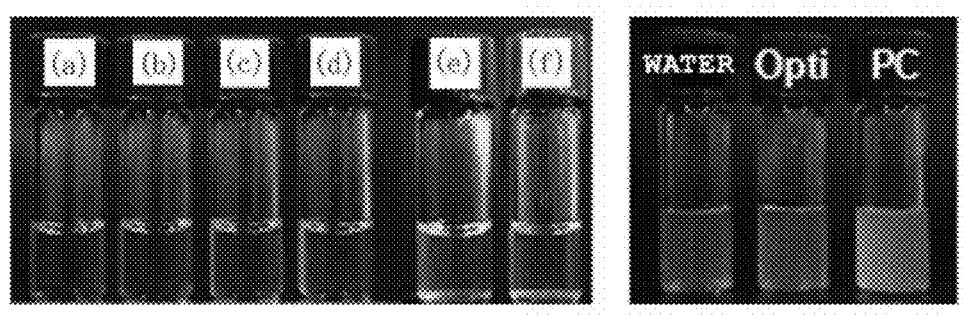
FIG. 21 is a photographic representation of agarose gel electrophoresis.
Figure 22:
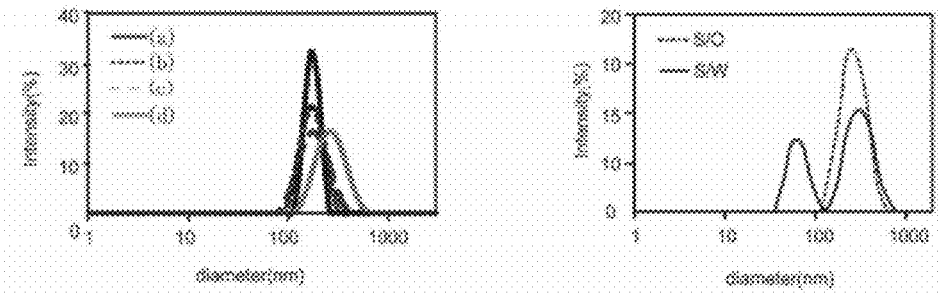
FIG. 22 is a graph representing the S/W particle diameter DLS.

FIG. 21 shows the state of the resulting EGFP-containing S/O and S/W. Sample (f) is the state after sample (e) was left unattended for 1 day. As shown in the photographs, EGFP-derived fluorescence was not observed in the S/O, except for samples (e) and (f) in which the suspension and precipitation of EGFP occurred. This is due to the concentration quenching resulting from the encapsulation of the EGFP in the carrier at high concentration. DLS measurement of the S/O particle size revealed that the particle size increased with decrease in ER-290 amounts with respect to the EGFP (Table 8, FIG. 22). This is the result of the increased EGFP amount per particle.

DLS particle size measurement revealed that the particle size was successfully reduced to less than 1 μm in the S/W produced with sample (d) that was able to encapsulate the largest amount of EGFP (Table 8, FIG. 22), though slight suspension was observed. The S/W showed two peaks. From the S/O particle size, one of the peaks is believed to be of the S/W complex with an average particle size of 325±21.8 nm, and the smaller peak is believed to be of positive micelles such as PC, DOPE, and R4-str. Further, zeta potential measurement revealed that the ζ potential was 35.1±1.1 mV, confirming that a significant portion of the particle surface charge was cationic.

TABLE 8

| Sample | (a) | (b) | (c) | (d) | S/W |
|---|---|---|---|---|---|
| Average particle size (nm) | 171 ± 8.3 | 174 ± 3.6 | 183 ± 12 | 272 ± 9.3 | 63.9 ± 1.4<br>325 ± 21.8 |

Experiment Example 12

Evaluation of EGFP-Containing S/W Cell Introducibility by R4-str Modification

The introducibility of EGFP into B16 cells was evaluated using a S/W modified with R4-str (stearyl tetraarginine) that improves cell introducibility, and with DOPE that exhibits the proton sponge effect in the endosome.

S/W samples were prepared in the compositions of Table 9 in the same manner as in Example 12. Note, however, that the EGFP-containing S/W was prepared by adding reduced serum medium (Opti-MEM), without adding Milli-Q water (5 mL) to the EGFP-containing S/W complex. B16 melanoma cells were prepared in $5\times10^5$ cells/ml in medium, and cultured overnight after being added to a cell 24-well plate in 1.0 ml/well ($5\times10^5$ cells/well). The cells were washed twice with 1.0 ml of PBS(−) after removing the medium. After washing the cells once with Opti-MEM (1.0 mL), the S/W of the compositions shown in Table 9, and 2× and 4× dilutions were added (1.0 mL each). The cells were cultured in a $CO_2$ incubator for 2 hours, and washed twice with 1.0 mL of PBS(−) after removing the solution. The medium was then exchanged to D-MEM. The state of the resulting cells was then observed with a fluorescence microscope, and the introducibility of EGFP into the cells was evaluated. As controls, the same experiments were conducted for samples unmodified with R4-str, and for untreated cells (non-treat), and the usefulness of R4-str was evaluated.

TABLE 9

| EGFP | ER-290 | DOPE | R4-str | PC | SOR |
|---|---|---|---|---|---|
| 100 μg | 1.1 mg | 7.5 mg | 6.0 mg | 7.5 mg | 182 mg |

Figure 23:
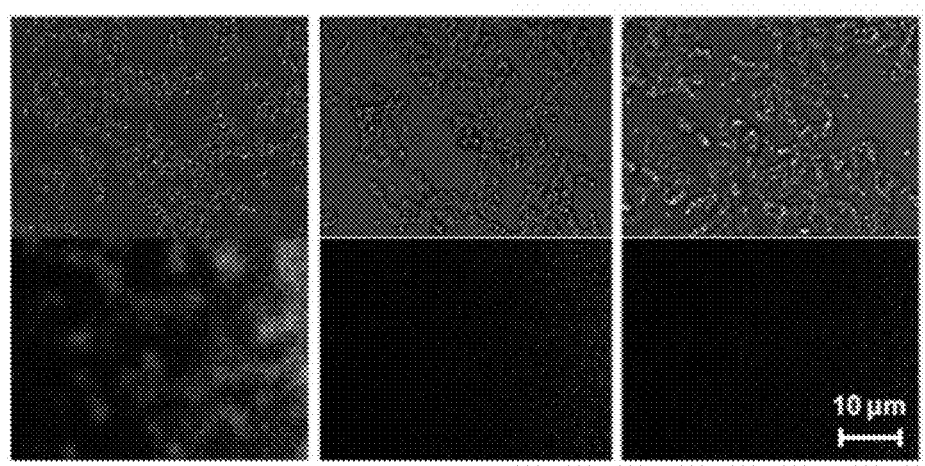
FIG. 23 represents fluorescence micrographs of S/W.

The results of fluorescence microscopy were the same for all samples, regardless of whether the samples were diluted. As an example, FIG. 23 shows the result of fluorescence microscopy for the sample diluted two times. The result confirmed that introduction of EGFP into the cells occurred only in the R4-str-modified S/W, and that R4-str was essential for the EGFP introduction into the cells. Because the cell surface is known to be typically anionic, the successful introduction is believed to be due to the effect of R4-str cationizing the carrier surface.

The invention claimed is:

1. A process for producing a drug delivery carrier that includes a water-soluble drug double-coated with two types of inner and outer surfactants 1 and 2, the process comprising the steps of:
   1) mixing and agitating a water-soluble drug-containing aqueous phase with an oily phase containing the surfactant 1 to form a W/O emulsion in which the water-soluble drug-containing aqueous phase is dispersed in the oily phase;
   2) removing the inner aqueous phase from the W/O emulsion to form a S/O in which the water-soluble drug coated with the surfactant 1 is dispersed in the oily phase;

3) mixing and agitating the S/O with an aqueous phase containing the surfactant 2 to form a S/O/W emulsion in which the S/O is dispersed in the aqueous phase; and 4) removing the inner oily phase from the S/O/W emulsion to form a S/W in which the water-soluble drug coated with the surfactant 1 and the surfactant 2 is dispersed in the aqueous phase, wherein the inner surfactant 1 is at least one member selected from the group consisting of: sucrose erucate ester and sucrose laurate ester; and the outer surfactant 2 is at least one member selected from the group consisting of: PC, sucrose laurate ester L-1695, PEG (2K)-DSPE, PEG(5K)-DSPE, PEG(comb)-DSPE, polysorbate 80, sodium dodecyl sulfate, and glycerin fatty acid ester.

2. The drug delivery carrier producing process according to claim 1, wherein the inner aqueous phase and the inner oily phase are removed by freeze drying.

3. The drug delivery carrier producing process according to claim 1, wherein the S/O/W emulsion is formed with addition or without addition of any one of glycerine, and sorbitoltrehalose.

4. The drug delivery carrier producing process according to claim 1, wherein the S/O is formed in such a manner that at least one of hydrophobic molecules such as DOPE and dinitrochlorobenzene, and cationic polymers such as PEI and poly-L-lysine is contained in the S/W emulsion.

5. The drug delivery carrier producing process according to claim 1, wherein the S/W is formed in such a manner that a cell membrane protein binding domain, including alkylated transmembrane peptides (for example, such as stearyl octaarginine R8-str, and stearyl tetraarginine R4-str), N-hydroxysuccinimide-PEG(2K)-DSPE, N-maleimide-PEG (2K)-DSPE, N-hydroxysuccinimide-PEG(2K)-DSPE, and antibodies, saquinavir, and hyaluronic acid modified by these, is contained in the S/O/W emulsion.

* * * * *